United States Patent
Heil, Jr. et al.

(10) Patent No.: US 6,473,633 B1
(45) Date of Patent: Oct. 29, 2002

(54) REMOVABLE CAP FOR TISSUE-INSERTABLE CONNECTIONS

(75) Inventors: Ronald W. Heil, Jr., Roseville, MN (US); Gregory R. Ley, New Brighton, MN (US); Dwight Skinner, Roseville, MN (US); Larry L. Hum, Cottage Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/363,477

(22) Filed: Jul. 29, 1999

(51) Int. Cl.[7] ............................................. A61B 5/042
(52) U.S. Cl. ...................................... 600/375; 607/127
(58) Field of Search ................................. 600/151, 200, 600/375, 208; 607/122, 125, 126, 127, 131; 427/2.12; 128/834; 604/287, 288, 265; 424/426, 433; 606/108, 76

(56) References Cited

U.S. PATENT DOCUMENTS

| | | | | |
|---|---|---|---|---|
| 2,603,217 A | * | 7/1952 | McShirley | 604/265 |
| 2,691,373 A | * | 10/1954 | Bried | 604/265 |
| 4,026,303 A | | 5/1977 | Babotai | 128/418 |
| 4,827,940 A | | 5/1989 | Mayer et al. | 128/642 |
| 4,876,109 A | * | 10/1989 | Mayer et al. | 427/2 |
| 5,531,781 A | * | 7/1996 | Alferness et al. | 607/122 |
| 5,531,783 A | | 7/1996 | Giele et al. | 607/126 |
| 5,575,814 A | | 11/1996 | Giele et al. | 607/127 |
| 5,658,326 A | * | 8/1997 | Barsne | 607/126 |
| 5,860,916 A | * | 1/1999 | Pylant | 600/208 |
| 5,931,776 A | * | 8/1999 | Dotolo | 604/265 |
| 6,091,978 A | | 7/2000 | Johnson et al. | 600/375 |

FOREIGN PATENT DOCUMENTS

EP          0761254          9/1996      ............ A61N/1/05

* cited by examiner

Primary Examiner—David O. Reip
Assistant Examiner—Julian W. Woo
(74) Attorney, Agent, or Firm—Schwegman, Lundberg, Woessner & Kluth, P.A.

(57) ABSTRACT

A helical element for insertion into tissue comprises a helical element having an insertion end, a protruding end and an open central area within the wire, rods, filaments, cables or the like that form the helix. The helical element has at least its insertion end covered by a cap of a water-soluble or water-dispersible composition. The cap is provided with a surface shape in a cross-section in which surface variations are present in the cross-section which create a surface orientation where a line from the center of the cross-section can intersect the surface, and a line perpendicular to said radius at a point of intersection with said surface forms four quadrants, three of said quadrants containing water-soluble or water-dispersible cap material. There is either a hollow area within the composition within the open central area or the material is more porous than the remaining material. The helical element preferably comprises an electrical lead, such as a positive endocardial lead, with an electrode at the protruding or distal end of the lead.

The helical element may comprise any biocompatable material with sufficient structural integrity to provide a secure attachment to tissue in a patient. Where the helical element is also to provide an active (electrically active) function, the composition of the helical element should also be electrically conductive.

21 Claims, 2 Drawing Sheets

REMOVABLE CAP FOR TISSUE-INSERTABLE CONNECTIONS

BACKGROUND OF THE ART

1. Field of the Invention

The present invention relates to the field of insertable or implantable materials or devices in which the material or device is secured into the tissue of a patient through a helical or screw element which is secured into tissue or the like. In particular, the present invention relates to protective elements such as protective caps over a penetrating or pointed section of the material or device, wherein the protective element is capable of timely removal (as by dissolution) from the penetrating or pointed section during technical (e.g., medical) procedures.

2. Background of the Art

Many therapeutic or protective procedures for patients include the implantation of devices into a patient. Such implantations include drug delivery systems, electrostimulating devices (such as pacemakers or pain reduction devices), monitoring devices, electrical leads, electrodes, sensor elements, etc. These devices often have to be firmly secured within the patient to prevent movement of the device that would defeat or diminish its effectiveness. This is particularly true with electrical leads in pacing or defibrillation devices, which must be precisely located so that patient monitoring and electrical stimulation is effective. There are a number of different formats for the securement of electrical leads in patients, including, but not limited to, clips, sutured attachment, corkscrew-like inserts (referred to as helical inserts), and other conventional securement formats found in mechanical systems.

A preferred means of securing leads is the helical insert such as found in the Guidant Cardiac Rhythm Management (CRM) Sweet-Tip® Model 4269 bipolar endocardial lead. This lead comprises a helical element having a base side (proximal end) with an electrode and a sharp tip on an insert side (a distal end) of the element. The pointed end penetrates tissue when a rotating motion is applied to the helical element, causing the element to puncture and or screw into the tissue, advancing the proximal end towards the tissue. The proximal end may have a relatively flat or convex electrical plate, electrode, sensing element (e.g., semiconductor, circuit board, pressure plate, etc.) or contact, and the advancing of the helical element into the tissue brings the contact into firm position with the tissue. In pacing or defibrillating devices, the electrical discharge passes through the electrode and/or into the helical connecting element. In some leads, the helical element is coated with a thin insulating coating layer (which must also be biocompatible) to render the helical element inactive or passive (from the standpoint of discharge). Typical coatings could include ceramics, and polymers such as polyamides, polyimides, polyurethanes, silicone resins, polyacrylates, and especially poly-para-xylylene (e.g., Parylene C).

These types of devices may be inserted into a patient by a number of different medical procedures. The less invasive or traumatic the procedure, the more desirable is that procedure. For example, although the electrodes may be inserted by open chest surgery, the delivery of the electrode through catheterization techniques through arteries or veins is much more preferred. The difficulties involved with passing a sharp element through the vasculature of a patient can be readily appreciated, especially where the path can be tortuous. Further difficulties in passing a sharp element arise when medical procedures require passing the element through heart valve structures. To avoid damage to the patient, the Guidant CRM Sweet-Tip® Model 4269 bipolar endocardial lead provides a mannitol cap over the helical element in the lead. The mannitol cap provides a protective cover for the helical element which prevents the point of the helical element from scraping or puncturing interior walls of the vasculature, valve leaflets or other tissue during introduction of the element to the patient. The mannitol effectively dissolves during the procedure, depending on the placement of the electrode and other environmental factors, usually over the course of about 4 to 10 minutes. This practice of providing caps on the leads has been effective in preventing damage to the patient during the introduction of the lead. Improper use of the lead, as by unauthorized immediate or premature insertion, can lead to inadequate fixation, possibly resulting in dislodgement or unsatisfactory pacing.

There have been two areas identified by the present inventors where improvements may be made in the use of mannitol caps in the protection of helical leads or securing elements. First, because of the physical shape of the helical element, mannitol present within the core of the helix tends to be dissolved out more slowly than desirable from within the helix and adjacent any electrode at the proximal end of the helical element. Further, any slowly dissolving mannitol that does remain within the confines or central area of the helix may have a tendency to obstruct the advance of the helical element through the tissue until all of the mannitol in the core area has been removed. Second, the lack of consistent rates of dissolution of the caps from the helical element, for example where the lead was prematurely positioned into soft tissue, tends to require surgeons to wait for a maximum length of time to provide assurance of the cap dissolution and proper electrical contact. Any prolongation of implant time, as would be the case here, is highly undesirable. Although neither of these considerations affect the in place performance of the connected leads, the reduction in procedural time by reducing or eliminating these effects is desired.

SUMMARY OF THE INVENTION

Helical tissue connectors are provided with protective caps of an aqueous soluble or aqueous dispersible material wherein the exterior surface of the protective cap has areas extending from a forward end of the cap towards the rearward end which have smaller radii of thickness than adjoining areas on the surface which extend from a forward end towards the rearward end of the caps. The caps with this design feature may be more readily dissolved than caps with uniformly circular radii. These modified cross-section caps may also be combined in a cap with a hollow core or more soluble core (with respect to the composition of the cap) to further increase the rate of cap dissolution.

DETAILED DESCRIPTION OF THE INVENTION

Figure 1:
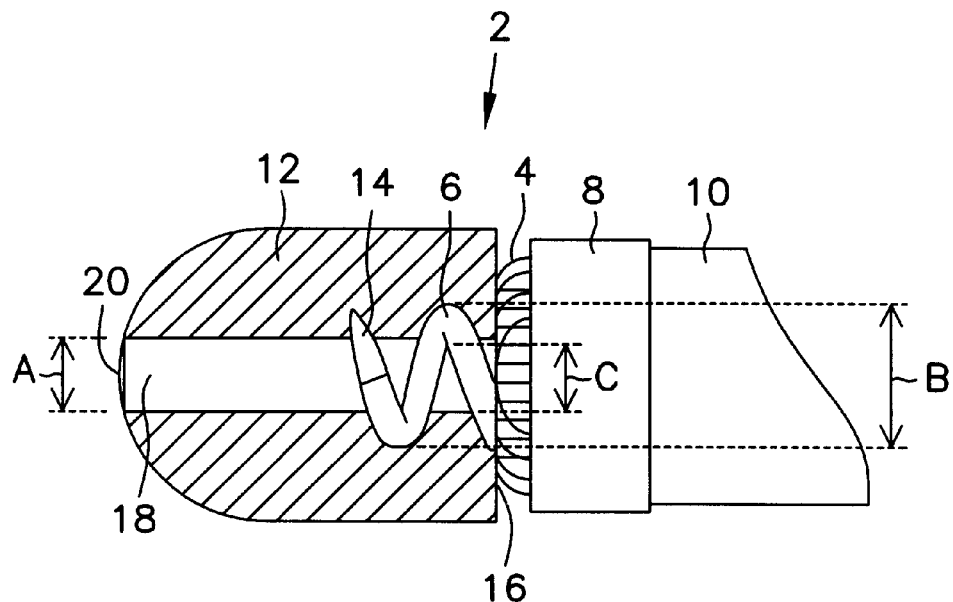
FIG. 1 shows an endocardial lead with a water soluble hollow cap.

The present invention describes a helical element, especially a helical element which can be securely inserted into electrical contact with the heart tissue. The helical element for insertion into tissue may comprise a helical element, an electrical contact, and a support for the electrical contact. The helical element has an insertion end (e.g., an end which is to be inserted to secure the element) and a protruding end. The protruding end (the proximal end with respect to a supporting element) protrudes from or is attached to an electrical contact or is part of the electrical contact. There is an open central area within the wire, rods, filaments, cables or the like that forms the helix of the helical element. The helical element has at least its insertion end covered by a cap of a water-soluble or water-dispersible first composition. The cap has indentations, trenches, grooves or the like which extend generally from a front end of the cap (distal end) to the rear end of the cap (the proximal end, being closest to the electrical contact or electrode). The indentations, trenches, grooves or the like (hereinafter referred to as a dissolution rate increasing surface feature) increase the surface area of the cap and thereby increase the rate of dissolution of the cap. There may also be a hollow portion of the cap, more thoroughly described herein, which by itself also decreases the time it takes to dissolve the cap so that it may be inserted into tissue earlier after catheterization or insertion into a patient. The open area within the helical element is either free of water-soluble or water-dispersible first composition or contains a water-soluble or water-dispersible second composition which dissolves more readily than the remainder of the first composition which forms the cap. For example, the second water-dispersible composition could be porous, fibrillated or the like, and composed of the same or different water-soluble or water-dispersible material as the first composition. The helical element preferably comprises an electrical lead, such as a positive fixation endocardial lead, with an electrode at the protruding or distal end of the lead.

The helical element may comprise any biocompatible material with sufficient structural integrity to provide a secure attachment to tissue in a patient. Where the helical element is also to provide an electrically active function, the composition of the helical element should also be electrically conductive. With these features in mind, a wide range of materials may be selected by the user for the helical element, including, but not limited to, metals, metal oxides, ceramics, polymeric materials, composite materials, reinforced materials, and the like. Metals such as Nitinol, titanium, Noble metal, gold, platinum, alloys (including Noble metal alloys), and the like are preferred.

As previously noted, the helical element may be coated with a protective or insulating layer to render the helical element either partially or completely inactive with respect to pacing discharges. Such coatings also should be biocompatible such as polymer coatings including polyamides, polyurethanes, silicone resins, polyolefins, polyimides, and especially poly-para-xylylene (e.g., Parylene C) and ceramic or composite coatings.

The composition of the cap material must meet the requirements that it is aqueous-soluble or aqueous-dispersible (blood being the aqueous system of choice for determining these physical properties). It is desirable that a 0.05 inch or 0.10 inch edge cube of the material in human blood at normal body temperature with light stirring should dissolve or disperse within ten minutes to meet this requirement. Natural sugars, saccharides, starches, other carbohydrates, polymers and the like are examples of materials which may be used for this cap material. It is particularly desirable that the cap material be non-toxic and preferably be biocompatible or even biodegradable or digestible.

For example, mannitol, iditol, glucitol, heptitol, octitol, arabinitol, bornesitiol, dambonitol, inositol, laminitol, ononitol, pinitol, sorbitol, low molecular weight poly(vinyl alcohol), low molecular weight poly(vinylpyrrolidone), soluble ethers, and soluble polyesters may be used in the practice of the present invention. Microfibers or biocompatible materials (e.g., microcellulose) held together by water-soluble water-dispersible binders may also be used in the practice of the present invention. Ingredients may also be present within these materials which increase the rate of dissolution, dispersion, erosion, or separation of the ingredients in the cap material, as is well known in the pharmaceutical tableting art.

It is also desirable in some circumstances to have the cap material carry active or therapeutic ingredients. For example, it is particularly desirable for the cap to carry anti-inflammatants, antibiotics, anticoagulants, antiarrhythmic medication, and the like within the composition. These can thereby be locally delivered as the helical device is inserted into the patient and as the cap, e.g., mannitol, dissolves.

FIG. 1 shows an electrode element 2 according to the present invention. The electrode element 2 comprises an electrode 4 having a helical securement element 6. The electrode 4 is carried on a collar or support 8 which is in turn carried on a catheter or lead body 10 for delivery. An aqueous-soluble or dispersible cap 12 covers the helical element 6 and especially a pointed end 14 on the helical element 6. The cap 12 also abuts or lies flat against the contact surface 16 of the electrode 4. A hollow core 18 within the cap 12 is shown. The hollow core 18 has an inside diameter A which is less than the outside diameter B of the helical element 6. This assures that the cap 12 is retained against movement away from the electrode 4. There is preferably, but not necessarily, a cover layer 20 over the opening to the hollow core 18 to prevent tearing of the cap or collection of unwanted material within the core 18 during positioning of the electrode element 2. The inside diameter A of the cap 12, the outside diameter (not specifically shown) of the electrode 4 and the collar 8 may be within the same general range of values, at about at least 0.001 inches, preferably from 0.002 to 0.25 inches or 0.005 to 0.20 inches, and more preferably from 0.005 to 0.100 inches. The helical element 6 may generally have an outside diameter B of about 0.01 to 0.07 inches, and an inside diameter C of from about 0.005 to 0.05 inches. The outside diameter is of course larger than the inside diameter at all times. The central area of the helical element 6 which is defined by the inside diameter C is where the hollow core 18 or the porous material (not shown) within the central area extends. The cap 12 may generally have a length within a range of, for example, 0.05 to 0.25 inches, preferably from 0.09 to 0.15 inches, and more preferably from 0.095 to 0.135 inches. In place of the hollow core 18, a core of more readily dissolvable material (e.g., powdered, frothed or foamed mannitol or equivalent functioning soluble material), may be present. The helical element 6 will have an outside diameter of the dimensions previously noted. It is desirable that the mass of the cap 12 extends below the outside diameter of the helical element 6 rather than merely extending to that outer diameter so that there is some physical gripping by the material of the cap 12 within the helix itself. It is preferred that the mass of the cap extend between the outside diameter and inside diameter of the helical element 6, but it may extend beyond the inside diameter of the helical element 6 and still show improved dissolution rate benefits.

Figure 2:
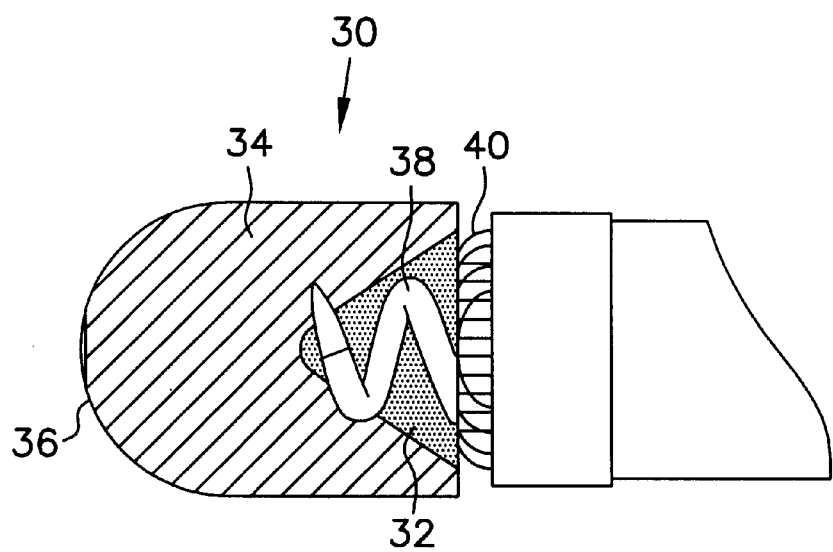
FIG. 2 shows an endocardial lead with a partially dissolved water soluble solid cap.

FIG. 2 shows an electrode element 30 of the prior art with a partially dissolved cap 32. The shaded area 34 represents material from the original cap 36 that has dissolved away, leaving the residue 32 within the helical element 38. It can be readily seen that the remaining core 32 would not only delay the ability of the helical element 38 to be inserted into tissue easily, but also that it would delay the time when the electrode 40 would be in flush electrical contact with tissue (not shown). As the cap would completely dissolve, the temporary presence of these materials merely delays the time when the electrode can be completely secured, but of course, does not affect its actual performance adversely otherwise. When the cap is prematurely positioned within soft tissue, a mass of mannitol may remain on the tip of the helical element as the last to dissolve material, as opposed to being on the core. This is one reason why the use of a thin cover over the opening to the core is optional.

Figure 3:
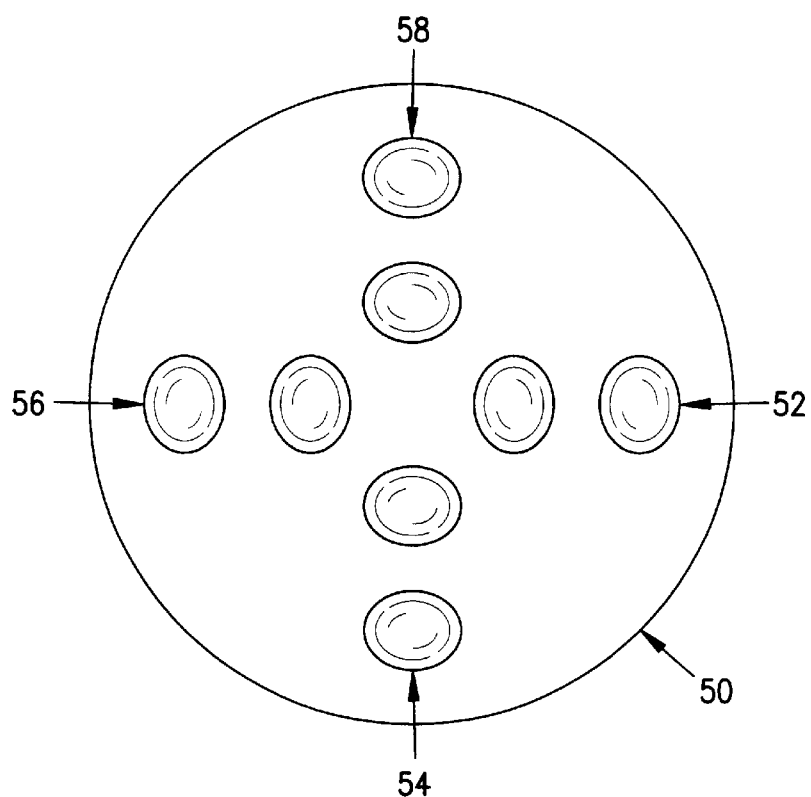
FIG. 3 shows a head-on view of a water soluble cap with dissolution exposing trenches along its length.

FIG. 3 shows a head-on view of a cap 50 having four trenches or grooves 52, 54, 56 and 58 on the outside surface of the cap.

Figure 4:
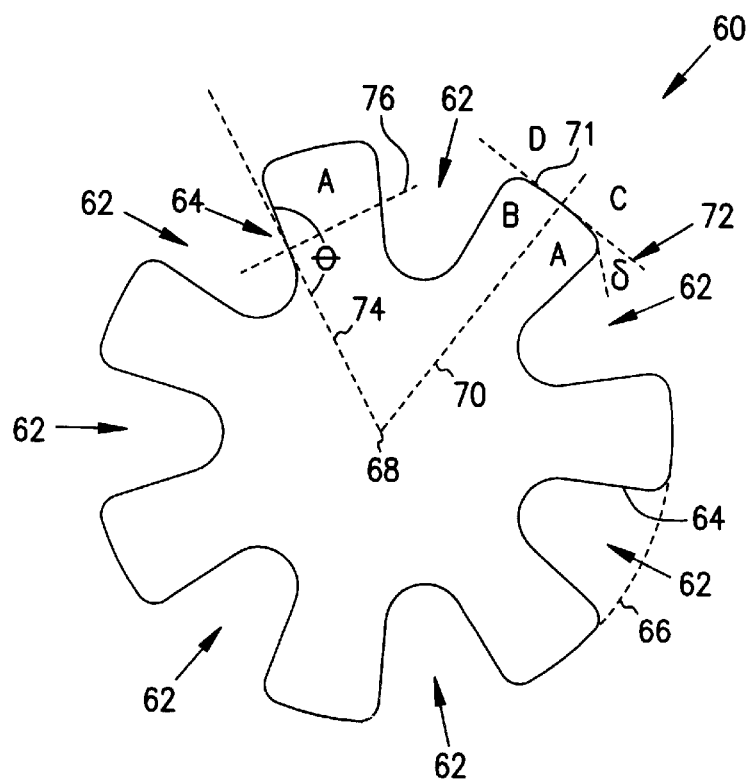
FIG. 4 shows a cross-section of a water soluble cap having a multiplicity of grooves molded into the cross-section of the cap.

FIG. 4 shows a cross-section of a cap 60 having a multiplicity (here 7) of grooves 62 molded into the cross-section of the cap 60. The grooves 62 have a groove interior surface 64 which provides a surface area which is larger than the surface area which would have been provided by a circular surface 66 in a uniformly circular surface area. This construction, therefore, requires the dissolution of less material to expose the helical insertion tip and provides a larger surface area of the soluble material to speed up dissolution of the cap 60 material which is present on the tip (not shown).

In summary, the modification of the surface of the soluble or dispersible cap according to the present invention is effected by providing a cap in which the surface of the cap on the exterior of at least 25% of the cross-section along its length has a non-continuous curvilinear shape (e.g., does not provide a circular, oval, straight-line or curve line positive polygon, with all angles on the end of a radius from the center of the cross-section to the surface having an angle below a line perpendicular to the radius at the point of intersection with the surface of the cap. This can be seen again in FIG. 4. The cross-section of the cap 60 has a center 68. A radius 70 extends from the center 68 to an area of surface 71 which has not been grooved and is therefore approximately round. A line 72 is drawn perpendicular to the radius 70 at the surface 71. Because the surface 71 is round, the surface is perpendicular to the radius 70 and angles away from the perpendicular line 72 to form an angle, alpha, which is less than ninety degrees and intermediate the right angle formed between the line 72 and the radius 70 and which includes a volume of the cap therein. On the other hand, a second radius 74 extending from the center 68 to a surface 64 within a groove 62 forms an angle theta with respect to the radius 74 which is greater than ninety degrees, and a quadrant A formed by the intersection of the radius 74 and a perpendicular line 76 at the intersection with the groove surface 64 is a third quadrant which contains cap material, while with the four quadrants formed by radius 70 and perpendicular line 72 at the rounded surface area 71 has cap material within only two quadrants A and B. Therefore, the surface configuration which is used in the practice of the present invention provides a surface shape in a cross-section in which surface variations are present in the cross-section which create a surface orientation where a line from the center of the cross-section can intersect the surface, and a line perpendicular to said radius at the point of intersection with said surface forms four quadrants, three of said quadrants containing water-soluble or water-dispersible cap material. This configuration would not be provided with a smooth cross-section (e.g., uniformly arcuate or circular or ellipsoidal, or oval, or positive angle polygonal) on the cap.

The grooves which increase the surface area of the cap and reduce its mass may also be in the form of grooves which individually do not pass along the length of the cap. The grooves may be circular or elliptical or oval, centered about the longitudinal axis of the cap. For example, the grooves may be circular indentations spaced at regular or irregular intervals along the length of the cap. The indentation of the groove therefore does not actually move parallel to the central axis of the cap. A skewed groove, e.g., oval, which also does not completely move along the length of the cap, may also be used. The grooves do not have to be uniform in the depth of the groove, nor do the grooves even have to be continuous.

The article of the present invention may be manufactured as follows. A conventional electrode with a helical insertion tip may be used. A cap may be molded with the appropriate outside dimensions and shape for the cap (including the grooves or trenches). The optional but preferred hollow section of the cap may then be performed, as by drilling, etching or molding of the appropriate dimensions for the hole (being less than the outside diameter of the helical element). Additionally, a cap may be molded with a hole in the cap material (e.g., as by macaroni extrusion of a continuous tube or molding of the cap with a removable rod inserted where the hole is desired, with the rod removed after formation of the cap, leaving a hole where the rod was removed), with cap sections cut off, and ends of the cap (where desired) closed off to form a closed cap. A Teflon or other release surface center core may be used to mold or extrude the cap material. Where the caps are first molded and a hole added, the hole may be added by selective dissolution of the material to form the hole, drilling or excavating of the hole, or pressing of a heated element into the cap material to remove material. Any method which is capable of producing the caps may be practiced in the present invention. After formation of the cap, the helical element is inserted into the cap, as by twisting or direct line pressure. The cap may be alternatively formed by the following procedures. The helical element is fitted with a removable rod within the core of the helix. A Teflon rod is desirable to assist in the ease of removal. The helical tip with the core therein is dipped or otherwise coated with the dissolvable material. After the cap has been formed by addition of the material onto the tip, the rod is removed. This leaves a hollow core within the helix as desired within the present invention. A more soluble material could be inserted into the helix either by first applying a limited amount of the more soluble material to fill the core of the helix, by pouring the more soluble material into an existing hole (as created by the removal of the rod), or by using a removable rod of more soluble material and not removing it.

Where a porous material is present within the core, rather than a hollow area, the core may either be first formed and the remainder of the cap built upon the porous core or a core excavated from the cap and the porous material added to the hollow area.

One beneficial aspect of the performance of the hollow-core caps of the present invention is the more direct control that the technician has over the timing of the use of the electrodes in the present invention. Not only does the cap dissolve off of the helical element more rapidly, but once there has been partial dissolution of the cap, the forces used to insert the helical element into the tissue cause the residual cap material to break off. When there was a core of material within the central area of the helix, that remaining material could not be broken off by the insertion forces. The technician would have to wait until the residual had been nearly completely dissolved away.

Body implantable, endocardial leads have been used for years to position sensing and stimulating electrodes within the human heart. Numerous electrode designs have evolved over this time. Typically, a lead design consists of a generally cylindrical lead body with a proximal connector end and a distal electrode end, separated by a conductor section suitably insulated from the body with a biocompatible insulating material. Also, numerous electrode fixation methods have been developed to insure prompt and stable positioning of the electrode within the heart. These fixation methods appear as tines, barbs, hooks, screws, etc., and are generally located at the distal end and in close proximity to the electrode. During implantation of the lead inside a patient, the electrode is advanced through the peripheral vasculature and into the heart chambers. As can be readily appreciated bullet shaped object of smooth profile will easily glide or otherwise pass through the vasculature. That same bullet shaped object will also pass easily among the internal structures, including valves, within the chambers of the heart. Positive fixation leads are so named to allow hook or screw-like features to actively or positively attach or fix to delicate internal structures. These design features provide the physician with the ability to attach the lead electrode in the site to provide the patient with optimal therapy. Although these exposed fixation features provide this and other advantages to the physician, accidental engagement including snagging of the fixation electrode within the vasculature or internal structures can occur. This disadvantage can be overcome through the use of fixation means that a) are retracted during the vascular passage of the electrode and subsequently deployed at the appropriate time or b) are covered by at least one soluble biocompatible fixation covering. The simplicity of the latter design over the former is well known in the industry.

The inventive cap design comprises an isolated distal electrode assembly composed of a soluble covering, typically consisting of mannitol, positioned over a stimulating electrode and fixation helix assembly (usually not retractable, but a cap may be provided over a retractable assembly). Also present is a plurality of surface features or, in this case, grooves upon the soluble covering. The purpose of these surface features, texturization, or grooves is to increase the surface area of the covering and subsequently increase the speed of dissolution. As previously described, a plurality (specifically, four in this case) of grooves is positioned upon the soluble covering. Each groove characterizes a finite amount of removed soluble covering defined by a phantom surface, two groove walls and the length of the soluble covering, or the diameter of the soluble covering.

This system of grooves hastens the dissolution of the soluble covering through at least three independent means. By a first means, the total amount of soluble covering comprising the encapsulation is simply reduced compared to an non-grooved covering. It is reasonable therefore that a small covering will require less time to dissolve than a larger covering. By a second means, the covering surface area is increased in a grooved configuration over that of a non-grooved configuration. Since dissolution occurs at the exposed surface of a particle, it is reasonable that a particle or covering of high surface area will dissolve sooner than a similar particle or covering with a smooth exposed surface area. Therefore, the use of a at least grooved soluble covering will dissolve sooner for these two independent means than a non-grooved covering. By a third means, the speed of dissolution will actually increase with time over a portion of the dissolution process since a grooved surface will expose an increasing surface area for dissolution.

Methods to prepare such high surface-area, texturized, or grooved coverings may vary. Examples of such methods include at least a) mechanical sculpting with Dremel-like tools, b) roughing through the use of abrasive techniques such as files or sandpaper, c) techniques which apply localized heating (soldering iron) to selectively volatilize the covering material, or d) a modified heated forming fixture, similar to a currently employed forming fixture, which imparts a well defined pattern upon the covering. In some cases, a combination of these methods may be employed. For purposes of generating highly reproducible coverings at a high volume, it appears that example describing a heated forming tools is most useful. The tool provides a cavity predominantly formed by a polymeric material of considerable heat insulative properties. At least one heated tapered shaping pin is positioned to extend to the interior region of the complete cavity formed when the two sections of the tool in this example are clamped together. For the grooving operation, a completed electrode is slowly inserted into the cavity. During this insertion, two grooves will be scribed into the mannitol covering to a fixed or known depth. After withdrawal, this first grooved electrode covering can be reinserted at, for example, a 90 degree orientation to the first insertion to provide a second set of grooves appropriately oriented. Additional grooves can be scribed by simply reorienting the electrode and repeating the operation. It must also be stated that additional shaping pins can be positioned within the tooling to scribe a greater number of grooves with a single operation. Finally, a shaping fixture may also be provided which will accomplish both bullet shaping of the rough mannitol covering and multiple scribing in a cap surface.

The elegant work described above for providing a mannitol protective covering with a open interior, "hollow core" is useful in combination with the surface treatment of the present invention. The time needed for complete dissolution with the hollow core should be and has been shown to be shorter than the dissolution time with a non-hollow covering. The exterior surface of the covering is not addressed in that earlier disclosure. The subject of this disclosure addresses the exterior surface of the covering. It is believed, therefore, that the dissolution enhancement provided by this disclosure can be combined with the dissolution enhancement provided by the hollow core design. It is anticipated that the resultant combined covering design will provide superior dissolution enhancement when compared to each of the two designs separately.

What is claimed:

1. A device for insertion into tissue comprising a helical element with an open central area and a water-soluble or water-dispersible cap for said helical element, the cap for said helical element having a surface shape in a cross-section in which surface variations are present in the cross-section which create a surface orientation where at least one radius comprising a line from a center of the cross-section intersects a surface of the cap at a point of intersection, and a line perpendicular to said at least one radius at the point of intersection with said surface forms four quadrants, three of said four quadrants containing water-soluble or water-dispersible cap material extending from the point of intersection, wherein said surface variations are located on the cap in a position such that, when the device is inserted into a body, said surface variations are only exposed to substances external to the cap to dissolve the cap, and wherein the surface variations increase a surface area of the cap as compared to a cap of the same maximum outside diameter of the cross-section without such surface variations for decreasing the time for dissolution of said cap in water.

2. The device of claim 1 wherein said surface variations comprise grooves within a surface which would otherwise be circular in cross-section.

3. The device of claim 1 wherein said surface variations comprise grooves that have a longitudinal axis of the device as a geometric center of the groove.

4. The device of claim 2 wherein said grooves extend along at least 25% of a length of said water-soluble or water-dispersible cap from a front of said water-soluble or water-dispersible cap to a back of said water-soluble or water-dispersible cap.

5. The device of claim 3 wherein said grooves provide an increase in surface area for said water-soluble or water-dispersible cap as compared to a water-soluble or water-dispersible cap without grooves.

6. The device of claim 1 wherein the cap for said helical element has a hollow area which overlaps at least a part of said open central area or a porous water-soluble or water-dispersible composition within at least a portion of said central area.

7. A device for insertion into tissue comprising a helical element with an open central area and a water-soluble or water-dispersible cap for said helical element, the cap for said helical element having a hollow area which overlaps at least a part of said open central area, and there are indentations in an outer surface of said cap which decrease the time for dissolution of said cap in water as compared to a cap of the same maximum outside diameter of cross-section without such indentations.

8. The device of claim 7 wherein said helical element is attached to an electrode.

9. The device of claim 8 wherein said helical element is coated with an electrically insulating, biocompatible material.

10. The device of claim 7 wherein said cap comprises a water-soluble or water-dispersible carbohydrate.

11. The device of claim 7 wherein said cap comprises a water-soluble or water-dispersible material selected from the group consisting of mannitol, iditol, glucitol, rabitol, heptitol, octitol, arabinitol, betitol, bornesitiol, dambonitol, inositol, laminitol, ononitol, pinitol, sorbitol, and aqueous-soluble organic polymers.

12. The device of claim 7 wherein said cap comprises mannitol.

13. A device for insertion into tissue comprising a helical element with an open central area and a water-soluble or water-dispersible cap for said helical element, the cap for said helical element having 1) at least a part of said open central area filled with a composition which is more readily dissolved or dispersed than a porous water-soluble or water-dispersible composition used for the structure of the water-soluble or water-dispersible cap, and 2) grooves along a surface of said cap, wherein said grooves are located on the cap in a position such that, when the device is inserted into a body, said grooves are only exposed to substances external to the cap to dissolve the cap.

14. The device of claim 13 wherein said grooves extend at least 25% of a length of said cap from a front end of said cap to a rear end of said cap.

15. The device of claim 13 wherein said grooves are circumferential about said cap and individual grooves do not extend the length of the cap.

16. A device for insertion into tissue comprising a helical element within an open central area and a water-soluble or water-dispersible cap for said helical element, the cap for said helical element having a surface shape in a cross-section which varies by both increasing and decreasing its diameter at different cross sections taken along the length of the cap, with at least two relative increases and at least two relative decreases, wherein said relative increases and relative decreases are located on the cap in a position such that, when the device is inserted into a body, said relative increases and relative decreases are only exposed to substances external to the cap to dissolve the cap.

17. The device of claim 16 wherein the surface shape cross-section variations comprise grooves that have a longitudinal axis of the device as a geometric center of the groove.

18. The device of claim 17 wherein said grooves are circumferential about said cap and individual grooves do not extend the length of the cap.

19. A device for insertion into tissue, the device comprising:

a helical element; and a water-soluble or water-dispersible cap for said helical element;

wherein, the cap for said helical element having grooves along a surface of said cap which decrease the time for dissolution of said cap in an aqueous solution as compared to a cap of the same maximum outside diameter of cross-section without said grooves, wherein said grooves are located on the cap in a position such that. when the device is inserted into a body, said grooves are only exposed to substances external to the cap to dissolve the cap, and wherein the water-soluble or water-dispersible cap is dissolvable in approximately 10 minutes or less after exposure to the aqueous solution.

20. The device of claim 19, wherein the cap comprises a water-soluble or water-dispersible material selected from the group consisting of mannitol, iditol, glucitol, rabitol, heptitol, octitol, arabinitol, betitol, bornesitiol, dambonitol, inositol, laminitol, ononitol, pinitol, sorbitol, and aqueous-soluble organic polymers.

21. The device of claim 25, wherein the cap comprises mannitol.

* * * * *

UNITED STATES PATENT AND TRADEMARK OFFICE
CERTIFICATE OF CORRECTION

PATENT NO. : 6,473,633 B1
DATED : October 29, 2002
INVENTOR(S) : Ronald W. Heil, Jr. et al.

It is certified that error appears in the above-identified patent and that said Letters Patent is hereby corrected as shown below:

<u>Column 10,</u>
Line 42, delete "." and insert -- , --, therefor.

Signed and Sealed this

Third Day of June, 2003

JAMES E. ROGAN
*Director of the United States Patent and Trademark Office*